United States Patent [19]
Halvorsen

[11] Patent Number: 5,842,573
[45] Date of Patent: Dec. 1, 1998

[54] METHOD OF TRANSPORTING CELLS AND KIT USEFUL THEREFOR

[76] Inventor: Yuan-Di C. Halvorsen, 5128 Salem Ridge Rd., Holly Springs, N.C. 27540

[21] Appl. No.: 814,662

[22] Filed: Mar. 11, 1997

[51] Int. Cl.⁶ .................................................. B65D 85/00
[52] U.S. Cl. ........................... 206/569; 206/439; 53/246; 53/539; 422/61
[58] Field of Search ..................... 206/204, 523, 206/564, 569, 438, 439; 53/246, 420, 471, 539; 220/359; 422/61

[56] References Cited

U.S. PATENT DOCUMENTS

| | | | |
|---|---|---|---|
| 4,162,003 | 7/1979 | Bartos et al. | 206/569 |
| 4,482,053 | 11/1984 | Alpern et al. | 206/439 |
| 4,829,006 | 5/1989 | Smith et al. | . |
| 4,844,246 | 7/1989 | Harrison et al. | 206/461 |
| 4,872,723 | 10/1989 | Kopf | 206/564 |
| 4,919,888 | 4/1990 | Spence | 206/439 |
| 4,932,533 | 6/1990 | Collier | 206/569 |
| 5,166,187 | 11/1992 | Collombel et al. | . |
| 5,271,499 | 12/1993 | Van Horssen | 206/523 |
| 5,589,351 | 12/1996 | Harootunian | . |
| 5,593,880 | 1/1997 | Northam et al. | . |

Primary Examiner—Paul T. Sewell
Assistant Examiner—Luan K. Bui
Attorney, Agent, or Firm—W. Murray Spruill

[57] ABSTRACT

A method of transporting cells in culture commences with the provisions of a multiwell plastic plate, wherein at least one well contains a sample of cells. A sheet of sterile adhesive film is applied to the top of the plate with sufficient pressure to seal the sample of cells into the well. The sterile adhesive film and the multiwell plate are covered with a plate cover, with a flexible plastic pad being optionally inserted between the sheet of sterile adhesive film and the plate cover. This method can be practiced with a kit containing these components in a unitized package.

25 Claims, 2 Drawing Sheets

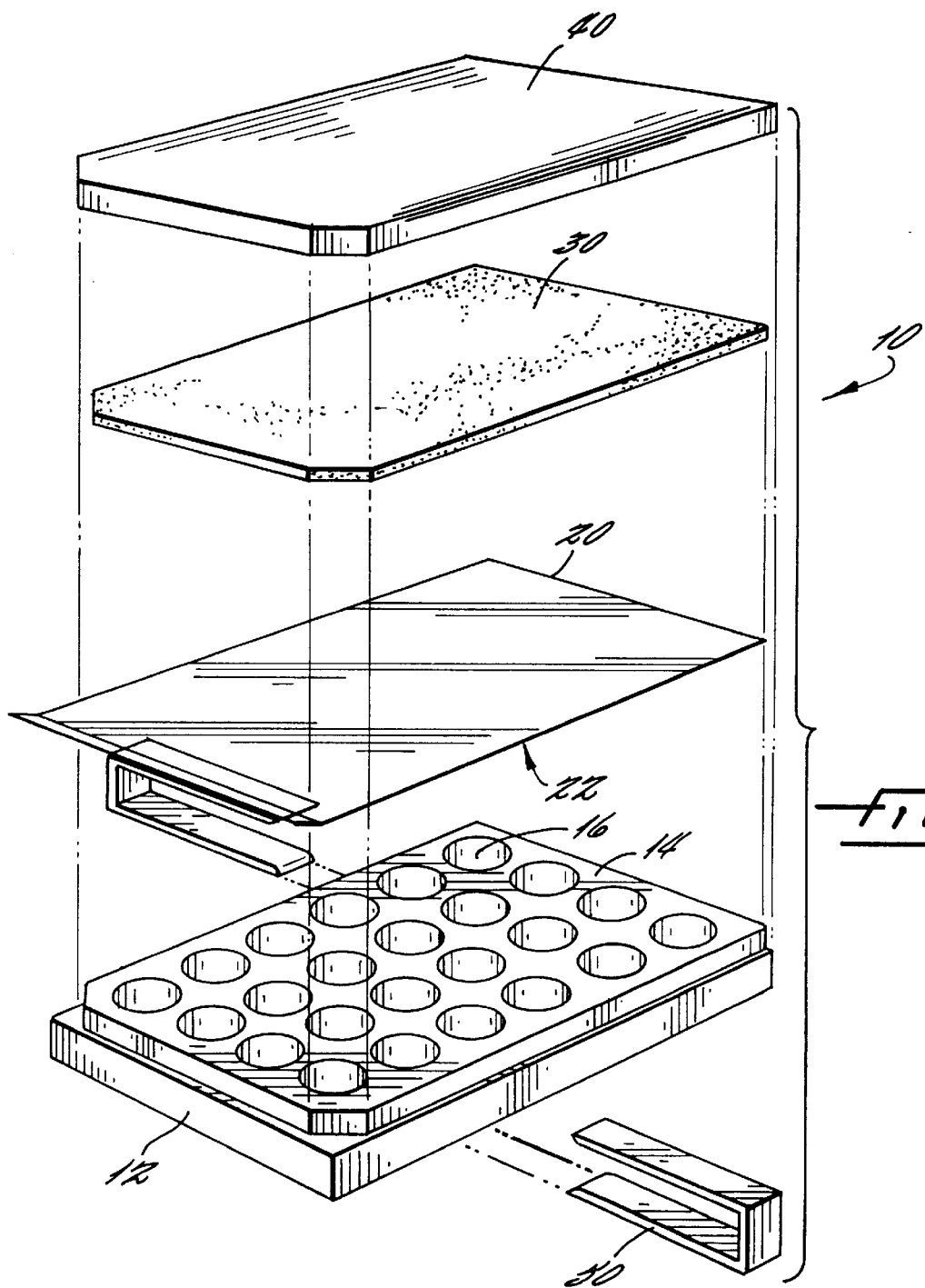

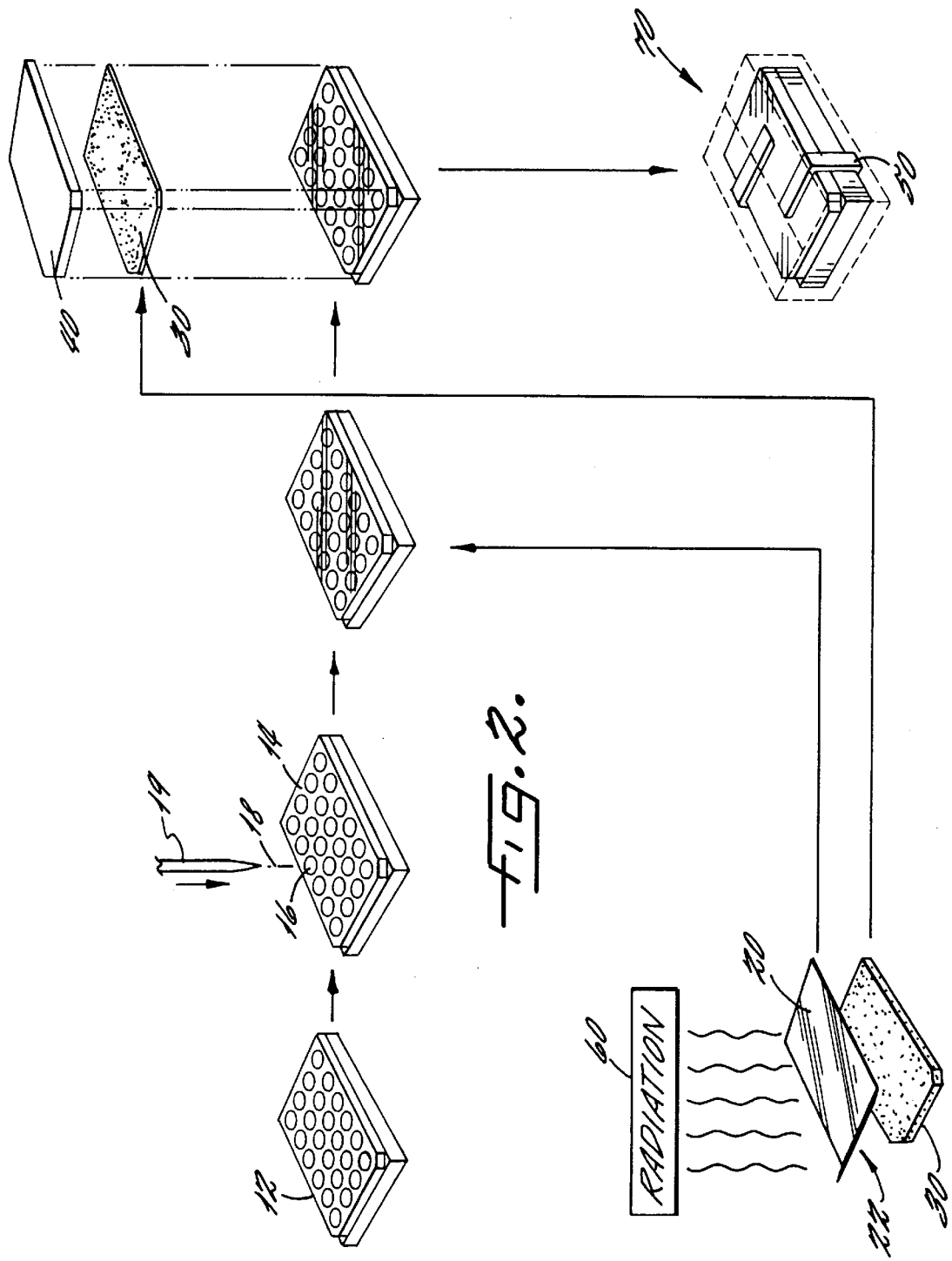

METHOD OF TRANSPORTING CELLS AND KIT USEFUL THEREFOR

FIELD OF THE INVENTION

This invention relates generally to maintaining cells in culture, and more specifically to methods of transporting cells in culture.

BACKGROUND OF THE INVENTION

Growing and maintaining living cells outside the original host source is achieved by cell (or tissue) culture. Living cells outside the original host source may be maintained in vitro through numerous passages if prepared and provided with the appropriate nutrients and conditions. Literally thousands of different cell lines have been initiated from the tissues of different species of animals, birds, insects, and plants, and are now in use in laboratories throughout the world.

Regardless of the cell system involved, the growth pattern of virtually all cells in culture is basically the same. Cell growth is dependent upon an appropriate nutrition and support system. Although cells may be grown successfully as a suspension, most cell cultures are preferentially grown as monolayers attached to a solid surface. Cell cultures may be grown in either test tubes or flasks, but the predominant use of cells is in the form of cultivated cell monolayers grown on the bottom of wells in plastic plates of various sizes (for example, 6, 12, 24, 48, or 96 wells per plate) previously seeded with cells in suspension. When appropriately treated, the plastic material of the plate supports the growth of cells in culture as monolayers on its surface. Once formed from the seeded cells, the cell monolayers are generally covered with a liquid growth or maintenance medium. In this form, the monolayers in the wells are ready for use.

Currently, many laboratories desiring such monolayers in multi-well plates for use in assays and the like must first obtain or produce cells in flasks or bottles. Wells in multi-well plates are seeded with the cells and allowed to grow to a desired number (generally sufficient to cover the bottom of the well surface). Then, after the cells are ready, the study material to be assayed is inoculated into the well. This procedure is both labor intensive and time consuming. Moreover, cells that have especially fragile cell membranes (e.g., adipose cells and the like) are likely to sustain damage or injury when being transferred from flask to well. If laboratories desiring such cell monolayers could obtain cell cultures in flat multi-well plates, in a ready-to-use form, then much time, effort and risk would be reduced. However, shipment of cell monolayers in wells using a liquid medium as a cover presents a problem, since shipment can cause spillage of the liquid medium, cellular disruption, and cross-contamination between wells. Some cells may grow in forms other than monolayers, but if their growth is promoted by adherence to the surface of the wells, the requirements for viable shipping needs are similar.

The present design of commercially available multiple well plates fails to provide convenient transport of these cells from one site to another without leakage or contamination. These plates are generally provided with a loosely fitting lid which allows gaseous exchange with the surrounding environment, but which does not seal the plate. Currently, individual well caps are available for 96-well plates. These plates can be prepared for transport by placing an individual cap over each well. Although generally provided as eight caps per strip, the time involved in placing the caps on and removing them is burdensome to those involved in handling such cells. In addition to being laborious, these known methods of sealing wells in multiwell plates promote accidental spilling of the tissue culture medium when lifting these caps, and adversely affect the maintenance of sterile conditions generally required for tissue culture work. Present methods are especially cumbersome when large number of tissue culture plates are to be transported. Moreover, there are currently no such caps manufactured for 6-, 12-, or 24-well plates, thus preventing the transport of cultured cells in these sterile plates.

It would thus be desirable to provide a convenient means for transporting or shipping cultured cells in multiwell plates, such that the cells and their respective media remain within each sterile well during shipping, and arrive at their shipping destination in a viable and useful form.

SUMMARY OF THE INVENTION

It is an object of the present invention to overcome the above-described difficulties and to provide a method by which cells may be transported and be ready for use by the end-user virtually immediately upon receipt. Accordingly, one aspect of the present invention is a method of transporting cells in culture. The method first involves providing a plastic plate with an upper surface comprising a plurality of wells, with at least one of the wells including a sample of cells. A sheet of sterile plastic film is then applied onto the upper surface of the plate. One surface of the sheet of sterile film includes an adhesive layer, and it is this adhesive layer that contacts the upper surface of the plate. This sheet of sterile film is applied to the upper surface of the plate with sufficient pressure to seal the well that includes the cell sample. The plate and the sheet of sterile film are then covered with a plate cover. If desired, the plate, the sheet of sterile film and the cover may be bound together by, for example, one or more binding clips. In addition, a sterile, flexible plastic pad may be inserted between the sheet of sterile film and the plate cover.

Another aspect of the present invention is a kit useful for transporting cells in culture. Such a kit comprises a multi-well plastic plate suitable for maintaining cells in culture, a sheet of sterile plastic film, wherein one surface of the sterile film includes an adhesive layer. The kit also comprises a plate cover and binding means for binding the plate, the sheet of sterile film, and the plate cover in a stacked relationship, as generally provided above. The kit additionally comprises packaging material configured to contain and unitize the plate, the sheet of sterile film, the plate cover and the binding means.

Yet a third aspect of the present invention is a transportable cell sample, comprising a multiwell plastic plate, with one well of the multiwell plate containing a sample of cells. The transportable cell sample further comprises a sheet of sterile film as described above, with the sheet of sterile film coextensively overlying the top surface of the multiwell plate and the adhesive layer contacting the top surface, such that the sample of cells is sealed into the well. The transportable cell sample additionally comprises a plate cover and binding means as described above.

Cells shipped in accordance with the present invention may be transported over long distances with virtually no adverse effects, spillage or cross-contamination between wells, with sterile conditions being maintained within each well throughout the shipping process. The present invention allows the transportation of an unlimited number of different cell types, as well as different cell lines, in the same carrier plate.

BRIEF DESCRIPTION OF THE DRAWINGS

FIG. 1 is an exploded view of a kit of the present invention, in which cells in culture may be transported.

FIG. 2 is a schematic diagram of a method of transporting cells in accordance with the present invention.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Referring now to FIG. 1, a kit 10 of the present invention first comprises a multiwell plate 12, with the multiwell plate 12 having an upper surface 14 containing a multiplicity of wells 16. The kit 10 further comprises a sheet of sterile film 20, with the sheet of sterile film 20 having an adhesive layer 22 on one surface thereof. In the illustrated embodiment of the invention, a sterile flexible plastic pad 30 is also included in the kit 10 to overlie the film 20. The kit 10 additionally contains a plate cover 40, and a pair of binding clips 50, which are configured to fit over the top of the binding cover 40 and the multiwell plate 12. The binding clips 50 or other binding means, such as a flexible strap, bind the plate 12, the film 20, the pad 30 and the cover 40 in a stacked relationship. The kit additionally comprises packaging material (not shown) for containing and unitizing the multiwell plate 12, sterile plastic sheet 20, sterile pad 30, plate cover 40 and binding clips 50.

The present invention is preferably used in conjunction with a sterile multiwell plate 12 that is presently available from a number of different commercial sources. The sterile multiwell plate 12 may vary in terms of shape, and may also vary in terms of the number of wells per plate (for example, such plates may contain 6, 12, 24, 48, or 96 wells). The plate 12 may be made of any suitable plastic material known in the art of cell culture. The most commonly used material for these containers is polystyrene, which is preferred. One example of a multiwell plate 12 that is suitable in the practice of the present invention is the 96-well plate (model number 25860) manufactured by Corning (Corning, N.Y. Other suitable plates are manufactured by Becton Dickinson (Franklin Lakes, N.J.; model number 3070) and USA/ Scientific Plastics (Ocala, Fla. model number 4616-7008). All such multiwell plates may be treated and handled in essentially the same way. Each multiwell plate 12 is individually wrapped and sterile. In use, each plate 12 is first removed from its package and kept closed until it is ready to be seeded with cells.

Sheets of plastic film 20 useful in the practice of the present invention are commercially available, and typically comprise polypropylene film. The film material is sufficiently rigid such that the film does not easily fold over each well, yet flexible enough to bend at the edges of the multiwell plate in order to sufficiently create a seal over each plate. One surface of the film is coated with an adhesive layer 22, which adhesive layer 22 contacts the upper surface 14 of the multiwell plate 12 in the method of the present invention. In accordance with the present invention, the adhesive is water- and heat-resistant in order to minimize potential leakage when plates are shipped via air freight with substantial pressure and temperature changes. In one embodiment of the present invention, the adhesive is acrylic-based.

The sheet of plastic film 20 useful in the present invention may be provided with a paper or plastic backing that is removed to expose the adhesive surface. Non-adhesive tabs at the edges of the sheet of film may be provided for convenient manipulation of the sheet of film when applying the sheet, and when removing the sheet after shipping. A particularly preferred sheet of plastic film useful in the present invention is Heat Seal Film™, available from USA/ Scientific Plastics (Ocala, FL).

While the application of the sheet of sterile plastic film 20 to the multiwell plate 12 may be sufficient to seal the wells 16 of a 96-well plate, the skilled artisan may find that the adhered area is insufficient to support the weight of the culture medium in plates with larger wells present in, for example, 6-, 12-, and 24-well plates. To seal wells 16 in such plates, the additional flexible plastic pad 30 can be provided to give extra support. The flexible pad 30 is positioned to overlie the sterile sheet of plastic film 20, after the sheet of film 20 has been applied to the multiwell plate 12.

In a preferred embodiment of the invention, the flexible pad 30 is a high-density polyethylene pad. Such pads are commercially available in a ⅛" thickness from, for example, the Nalgene Company (Rochester, N.Y.). The pads 30 are generally provided as large sheets or on large rolls. The skilled artisan may find it desirable to size and configure (by, e.g., cutting the large sheet) a pad 30 in order to coextensively overlie the sheet of sterile film 20, and additionally in order to shape and size the pad 30 such that the pad 30 nests inside the plate cover 40 as demonstrated in FIG.1.

The sheet of plastic film 20 and the flexible plastic pad 30 described herein are sterilized prior to being applied to the multiwell plate 12, in order to maintain sterile conditions in the wells 16 of the plate 12 during shipping of the plate 12. In one embodiment, the sheet of plastic film 20 and the flexible plastic pad 30 are sterilized by exposure to ionizing irradiation, and preferably gamma-radiation, although other forms of irradiation such as photon irradiation are suitable. The sheet of plastic film 20 and the pad 30 are exposed to the radiation for an amount of time sufficient to sterilize the film 20, but such that the adhesive characteristics of the adhesive layer 22 are not altered. Depending on the radiation source, the exposure to radiation will generally last for at least about 5 minutes, more preferably for at least about 10 minutes, and most preferably for at least about 15 minutes. The sheet of film 20 and the flexible pad 30 are exposed to a radiation dosage of at least about 5000 rads, more preferably a dosage of at least about 7000 rads, and most preferably a dosage of about 9000 rads. The radiation may be provided by any means known to one skilled in the art, including by exposure to $^{60}$cobalt or by a linear accelerator with an energy of from about four to about six MV.

Multiwell plates that are commercially available and are useful in the present invention are generally provided with a plate cover 40 that fits over the top of the multiwell plate 12, but which does not seal the plate wells 16. The plate cover 40 is useful in covering the sheet of sterile plastic film 20 after the film 20 has been applied to the top surface 14 of the plate 12. Usually, multiwell culture plates are provided with a cover designed with a gap of about 0.5 mm between the cover and the upper surface of the plate. In the practice of the present invention, it is preferred that the multiwell plate and the plate cover that the plate is commercially provided with be used together, although such a pairing is not required by the invention.

After the application of the sterile film 20 to the plate 12, but prior to covering the plate 12 with the plate cover 40, an O-ring or gasket can optionally be placed around the plate 12 in order to enhance the fit of the plate cover 40 onto the plate 12. The O-ring or gasket may be made of rubber, plastic, or metal, according to the desire of the skilled practitioner. Alternatively, strips or pieces of flexible plastic material can optionally be wrapped around the plate 12 prior to the covering of the plate 12 with the plate cover 40, in order to enhance the fit between the plate 12 and plate cover 40. The O-ring, gasket, or plastic material will preferably be sterilized prior to being placed around the plate 12, which sterilization may be performed by the methods described herein, or by any other suitable means known to one skilled in the art.

The multiwell plate 12, the sheet of film 20, the flexible plastic pad 30 (if desired) and plate cover 40 are preferably bound together with the binding clip 50 or other binding means in order to further minimize cell medium leakage from and between wells and in order to make shipping more convenient. The binding clip 50 may be made of plastic, metal, or any other material deemed acceptable by one skilled in the art. In a preferred embodiment, the length of the binding clip 50 is at least about half the width of the plate cover 40, such that the binding force is applied toward the center of the surface of the plate cover 40 and the plate 12. In addition, or in the alternative, the assembled multiwell plate 12, sheet of adhesive film 20, flexible plastic pad 30, and plate cover 40 may be wrapped edgewise or otherwise with a strip or sheet of elastic paraffin-based material (i.e. PARAFILMN), or other elastic means such as a flexible strap.

The kit 10 further comprises packaging material configured and suitable for containing and unitizing the plate 12, the sheet 20, the pad 30, the plate cover 40 and the binding clip 50 or other binding means. The packaging material can be, for example, a box or a sealable plastic bag, optionally containing padding or packing material to minimize movement within the kit during shipping.

FIG. 2 illustrates a method of transporting cells using the kit 10 of FIG. 1. In such a method, the multiwell plate 12 is provided and a sample of cells 18 placed in at least one well 16 of the plate 12. The sterile sheet of film 20 is applied onto the top surface 14 of the multiwell plate 12, with the adhesive layer 22 of the sheet 20 contacting the upper surface 14 of the plate 12. The sterile sheet of film 20 is applied with sufficient pressure such that the sample of cells 18 contained in the well 16 is sealed therein. In one embodiment of the invention, the sterile sheet of film 20 and the pad 30 are exposed to ionizing radiation 60 in order to sterilize the film 20 prior to applying the film 20 to the multiwell plate 12. After applying the sterile sheet of plastic film 20, the multiwell plate is covered with the sterile pad 30 and the plate cover 40. The multiwell plate 12, the sterile sheet of film 20, the sterile pad 30, and the plate cover 40 are bound together with the binding clip 50. Cells in culture are thus shipped according to the present invention in an assemblage represented, for example, by element 70 of FIG. 2.

The present invention is useful in transporting virtually any type of cell (e.g. animal, insect, diploid, heteroploid, etc.) that may be maintained in culture. These cells may be primary (first passage from the host) or serial (two or more passages from the original host), and are preferably provided in a well of the multiwell plate in the form of a monolayer, wherein the cells adhere to the plastic surface of the well. Regardless of passage number, cell monolayers transported by the method of the present invention should retain viability during the transportation process, although physiological changes from their in vivo state may occur.

The cells to be transported are typically first grown in large flasks or other containers. At a stage in the growth process when transfer is appropriate, the cells are re-suspended in growth medium to the desired number (typically, approximately greater than $1 \times 10^5$ cells per ml) and transferred to the wells of the multi-well plate. Transfer of cells may be accomplished by any means known in the art, but is generally accomplished by using a manual or automatic pipettor, designated at 19 in FIG. 2. Seeding of the desired number of cells is preferably accomplished under sterile conditions. The type of medium used on the cells prior to shipment may be of any composition that is consistent with adequate cell growth and the maintenance of good cell metabolism. Different wells or rows of wells may be seeded with different cell systems. When a cell monolayer is of acceptable density, as determined by the requirements of the recipient, seeded plates are ready for shipping. It will be appreciated that within the scope of the present invention, many cell types and/or cell lines will be able to be shipped together within the same multiwell plate, in that each well will be sealed off and isolated from other wells, without the risk of cross-contamination among the wells.

Many modifications and other embodiments of the invention will come to mind in one skilled in the art to which this invention pertains having the benefit of the teachings presented in the foregoing descriptions and the associated drawings. Therefore, it is to be understood that the invention is not to be limited to the specific embodiments disclosed. Although specific terms are employed, they are used in a generic and descriptive sense only, and not for purposes of limitation. Modifications and embodiments thereof are intended to be included within the scope of the appended claims.

That which is claimed:

1. A method for transporting cells in culture, comprising:
   providing a plastic plate, said plate having an upper surface comprising a plurality of wells, one of said wells including a sample of cells;
   applying a sheet of sterile plastic film onto the upper surface of said plate, wherein one surface of said sterile film includes an adhesive layer, said adhesive layer contacting said upper surface of said plate, said sheet of sterile film being applied with sufficient pressure to seal said well that includes said sample; and
   covering said sheet of sterile film and said plate with a plate cover.

2. A method according to claim 1, further comprising the step of binding said plate, said sheet of sterile film, and said plate cover together.

3. A method according to claim 1, further comprising positioning a sterile, flexible plastic pad upon said sheet of sterile film prior to said covering step.

4. A method according to claim 1, wherein said plate is a 96-well multiwell plate.

5. A method according to claim 1, wherein said sample of cells are provided as a monolayer.

6. A method according to claim 1, further comprising the step of exposing said sterile film to gamma radiation to sterilize said film prior to said applying step.

7. A method according to claim 1, wherein said adhesive is acrylic-based.

8. A method according to claim 3, wherein said sterile, flexible plastic pad is a polyethylene pad.

9. A method according to claim 3, wherein said sterile, flexible plastic pad is sized and configured such that said sterile, flexible plastic pad nests within an interior surface of said plate cover.

10. A method according to claim 3, further comprising the step of exposing said sterile, flexible plastic pad to gamma radiation to sterilize said plastic pad prior to said positioning step.

11. A method according to claim 1, wherein said binding step comprises applying at least one binding clip over said plate cover and said plate.

12. A kit for transporting cells in culture, comprising:
   a multiwell plastic plate, wherein said multiwell plate is suitable for maintaining cells in culture;
   a sheet of sterile plastic film, wherein one surface of said sterile film includes an adhesive layer;
   a plate cover;
   binding means, for binding said plate, said sheet of sterile film, and said plate cover in a stacked relationship; and
   packaging material configured to contain and unitize said plate, said sheet of sterile film, said plate cover and said binding means.

13. A kit according to claim 12, further comprising a sterile, flexible plastic pad, said pad being sized and configured to overlay said sheet of sterile film and nest within an interior surface of said plate cover.

14. A kit according to claim 13, wherein said sterile, flexible plastic pad is a polyethylene pad.

15. A kit according to claim 12, wherein said plate is a 96-well multiwell plate.

16. A kit according to claim 12, wherein said sheet of sterile film is sterilized by exposing said sheet of film to gamma radiation.

17. A kit according to claim 13, wherein said sterile, flexible plastic pad is sterilized by exposing said plastic pad to gamma radiation.

18. A kit according to claim 12, wherein said binding means comprises at least one binding clip that fits over said plate cover and said plate.

19. A transportable cell sample, comprising:
   a multiwell plastic plate, wherein one well of said multiwell plate contains a sample of cells;
   a sheet of sterile plastic film, wherein one surface of said sterile film includes an adhesive layer, said sheet of sterile film coextensively overlying a top surface of said multiwell plate and said adhesive layer contacting said top surface, such that said sample of cells is sealed into said well;
   a plate cover coextensively overlying said plate and said sheet of sterile film; and
   binding means for binding said plate, said sheet of sterile film, and said plate cover in a stacked relationship.

20. A transportable cell sample according to claim 19, further comprising a sterile, flexible plastic pad, said pad being sized and configured to overlay said sheet of sterile film and nest within an interior surface of said plate cover.

21. A transportable cell sample according to claim 20, wherein said sterile flexible plastic pad is a polyethylene pad.

22. A transportable cell sample according to claim 19, wherein said plate is a 96-well multiwell plate.

23. A transportable cell sample according to claim 19, wherein said sheet of sterile film is sterilized by exposing said sheet of film to gamma radiation.

24. A transportable cell sample according to claim 20, wherein said sterile, flexible plastic pad is sterilized by exposing said plastic pad to gamma radiation.

25. A transportable cell sample according to claim 19, wherein said binding means comprises at least one binding clip that fits over said plate cover and said plate.

* * * * *